United States Patent
Henderson et al.

(10) Patent No.: US 8,461,409 B2
(45) Date of Patent: Jun. 11, 2013

(54) VISCERA PROTECTOR

(75) Inventors: James Henderson, Gatineau (CA); Michael T. O'Malley, Almonte (CA)

(73) Assignee: Canica Design Inc., Almonte, ON (*) Notice: Subject to any disclaimer, the term of this patent is extended or adjusted under 35 U.S.C. 154(b) by 0 days.

(21) Appl. No.: 12/926,238

(22) Filed: Nov. 4, 2010

(65) Prior Publication Data
US 2011/0120477 A1 May 26, 2011

Related U.S. Application Data

(63) Continuation-in-part of application No. 12/076,010, filed on Mar. 12, 2008, now abandoned.

(51) Int. Cl.
*A61F 13/00* (2006.01)

(52) U.S. Cl.
USPC .............................. 602/41; 602/42; 128/850

(58) Field of Classification Search
USPC ............... 128/850, 887, 888; 602/42, 43, 47, 602/58–61; 424/443–449
See application file for complete search history.

(56) References Cited

U.S. PATENT DOCUMENTS

| | | | |
|---|---|---|---|
| 4,541,426 A | 9/1985 | Webster | |
| 5,000,172 A | 3/1991 | Ward | |
| 5,176,663 A | 1/1993 | Svedman | |
| 5,340,363 A | 8/1994 | Fabo | |
| 5,520,925 A * | 5/1996 | Maser | 424/443 |
| 5,605,165 A | 2/1997 | Sessions | |
| 5,645,081 A | 7/1997 | Argenta | |
| 6,794,554 B2 * | 9/2004 | Sessions et al. | 602/46 |
| 7,309,809 B2 | 12/2007 | Smith | |
| 7,932,429 B2 * | 4/2011 | Ragaru et al. | 602/41 |

* cited by examiner

*Primary Examiner* — Patricia Bianco
*Assistant Examiner* — Keri J Nelson
(74) *Attorney, Agent, or Firm* — Robert G. Hendry

(57) ABSTRACT

A composite viscera protector consisting of a silicone layer, a polypropylene mesh layer and an additional silicon layer having a thickness between 0.5 and 2.53 mm, with a repeating series of holes in a pattern over its entire surface or a portion thereof with the holes being slits on one or two planes non-intersecting and being of a size between 1 and 10 mm.

6 Claims, 3 Drawing Sheets

VISCERA PROTECTOR

This application is a continuation in part patent application of Ser. No. 12/076,010 filed on Mar. 12, 2008, now abandoned which claims priority of Canadian patent application 2,581,698, filed on Mar. 14, 2007.

FIELD OF THE INVENTION

The present invention relates to a viscera protector for use in surgery of the abdomen as a temporary bolster and protection of the bowel during the reduction phase of treatment of abdominal fascia hernia defect and other deficiencies in the fascia. The outer silicone material is non-adherent to tissue to minimize in growth, the internal mesh provides mechanical support and allows the sheet to be stabilized with a staple or suture and prevents the silicone from running or tearing. The perforations allow fluid to communicate and pass through the sheet and the aperture sizes are such as to allow fluid to pass, but to minimize the possibility of a bowel becoming entrapped. The viscera protector is considered to be flexible, non-adherent, conformal, strong, non-occluding and may be packaged as a sterile, single use, disposable unit, in a barrier package. The outer material consists of two layers of silicone. The inner layer of material preferably polypropylene mesh or fabric is formed into a multi-layer laminated sheet shaped square, rectangle or oval with rounded corners.

Suction tubes are provided for drawing away exudates from the wound. This kind of suction may be used to create the vacuum under the protector. If the protector is a flexible cover, which is typically more comfortable for the patient, some sort of porous packing may be provided under the cover to provide the space in which the vacuum is formed.

BACKGROUND OF THE INVENTION

As shown, for example in U.S. Pat. No. 5,645,081 a method of treating tissue damage is provided by applying negative pressure to a wound. The negative pressure is provided in sufficient duration and magnitude to promote tissue migration in order to facilitate the closure of the wound. U.S. Pat. No. 5,645,081 discloses a section covering the wound, a flexible hollow tube inserted into one end and attached to a vacuum pump at another end, an adhesive sheet overlying the section and tubing to adhere to the skin surrounding the wound in order to form a seal that allows the creation of a vacuum when the suction pump is operating. In a preferred embodiment, pressure is applied in 5 minute periods of application and non-application.

SUMMARY OF THE INVENTION

According to the present disclosure, a thin flexible member for use in a vacuum bandage is provided. The member includes outer surfaces, a wound contacting surface configured to be in contact with and conform to a wound surface of a wound. The member further includes a plurality of discrete holes formed in the wound contacting surfaces, a port, which communicates with a vacuum source, and communicating means between the holes and the port. The member is made from generally non-compressible material. Further, the material is generally transparent and porous and the outer members are of non-adhering material. An intermediate layer of mesh is laminated between the thin flexible members.

In some embodiments, the wound-contacting surface of the member includes apertures in the intermediate member rather than a mesh intermediate layer.

In some embodiments of the invention, the dressing member is adapted to be stapled or sutured to the wound area.

BRIEF DESCRIPTION OF THE DRAWINGS

In the accompanying drawings, which illustrate embodiments of the invention

DETAILED DESCRIPTION OF THE INVENTION

Figure 1:
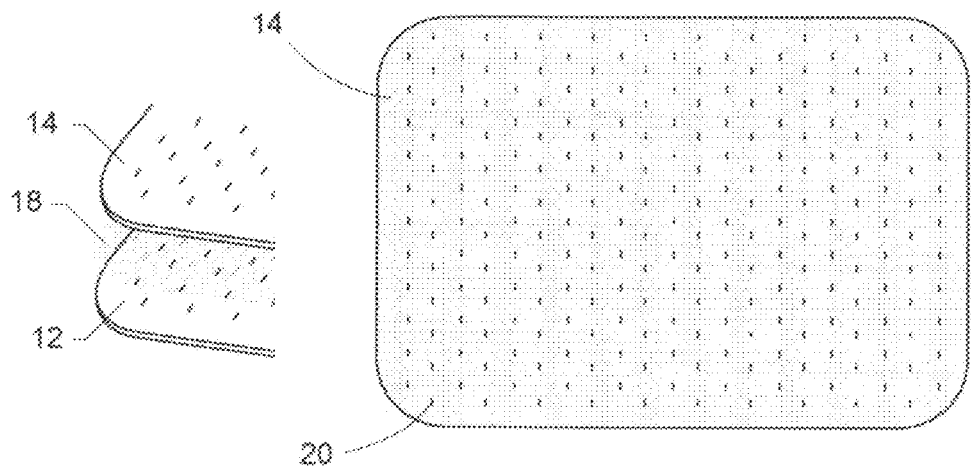
FIG. 1 is a top view and part diagrammatic view of a viscera protector.
Figure 2:
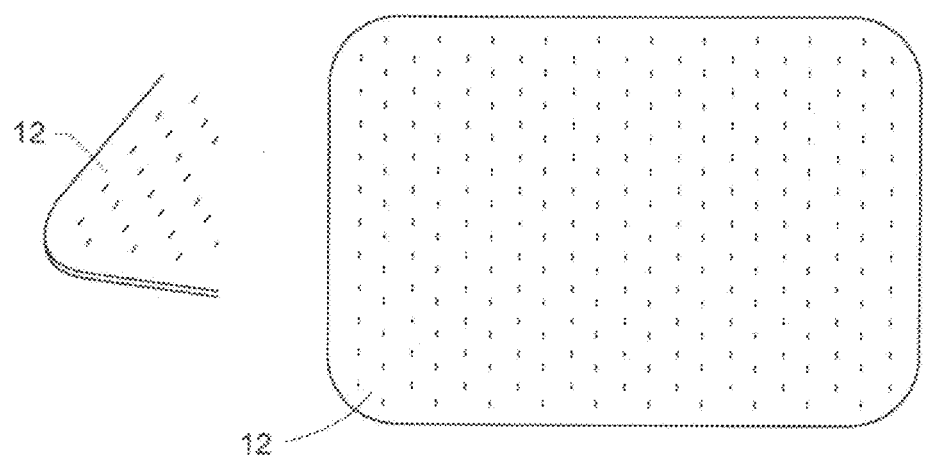
FIG. 2 is a top view of a sheet of the viscera protector.
Figure 3:
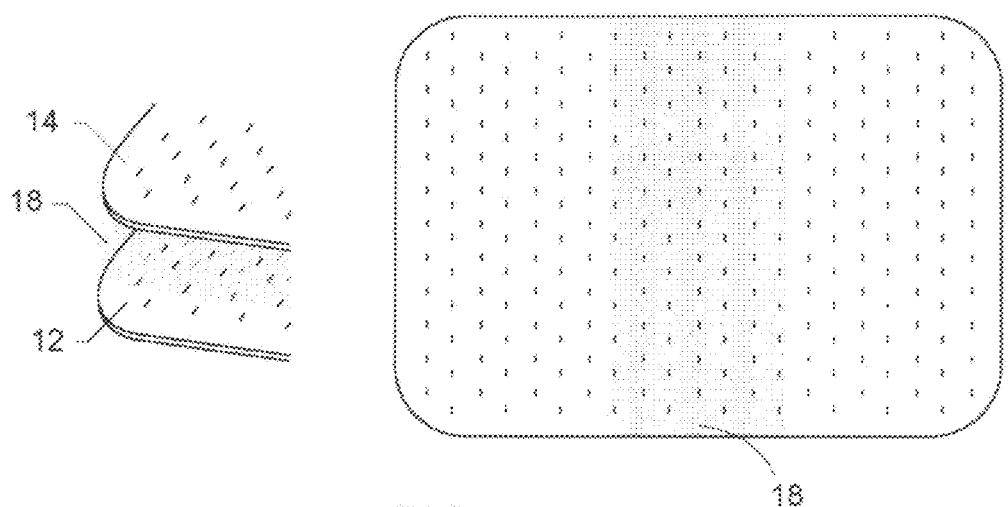
FIG. 3 is a top plan view of a second embodiment or variant.

The material of the viscera protector 10 includes outer layers 12 and 14 comprising two silicone sheets each having a thickness of between 0.5 and 2.53 mm or 0.1 and 2.53 mm and an intermediate inside layer 18 of polypropylene mesh or fabric of 0.02 to 1.5 mm of thickness. The viscera protector 10 is placed over the bowel, inside the abdominal wall, where it can be left free-floating in the abdomen or sutured in place. Holes or slits 20 sized between 1 and 10 mm are provided in patterns or repeating rows in the silicone sheets 12 and 14 and intermediate polypropylene mesh layer 18.

The composite, laminated construction layers include silicone layers 12 and 14 and intermediate polypropylene mesh layer 18. Silicone layers 12 and 14 are non-adherent and non-reactive. Inner mesh layer 18 bolsters the silicone layers 12 and 14 from tearing under point load created at the fastener or suture engagement points. Inner mesh layer 18 supports the holes or slits 20 and prevents the holes or slits 20 from becoming enlarged under load.

Controlling the size of holes 20 on silicone layers 12 and 14 is critical. If the holes or slits 20 enlarge, bowel tissue can be trapped in the holes and fistulas can result. Such a condition can be life-threatening. The size of hole 20 must be large enough to allow free passage of fluid and minimize restriction, but it must also be small enough to minimize the possibility of bowel entrapment. Allowing exudates or fluid to pass is also critical. As the post-surgical inflammatory response subsides, fluid leaves the inflamed abdominal tissues and enters the airspace within the abdomen. This fluid must be drained because it is a coagulant and proven to support rapid colonization by anaerobic-septic-bacteria. Fluid or exudates must freely exit or be drained to the outside of the patient's body passively or actively as by a tube 24 so as to maintain an ascetic abdominal environment. An occluding sheet member would restrict fluid flow.

The pattern of holes or slits 20 in silicone layers 12 and 14 is arranged to provide support to the bowel while providing adequate fluid communication. The pattern does not allow the layers 12 and 14 to form creases under elastomeric load. The slit pattern is arranged such that under elastomeric load the protector 10 does not fall into a rut or form a trough.

The preferred material for layers 12 an 14 is silicone as it is biologically inert, non-adherent to bowel and other tissues when placed in the paracolic gutter. Silicone also prevents adhesions between tissue layers.

Figure 5:
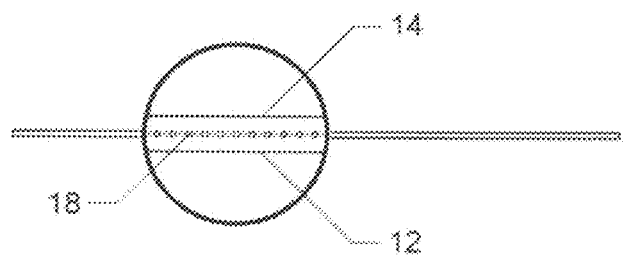
FIG. 5 is an end view of the viscera protector of FIG. 2, of which a portion is enlarged for clarity.
Figure 4:
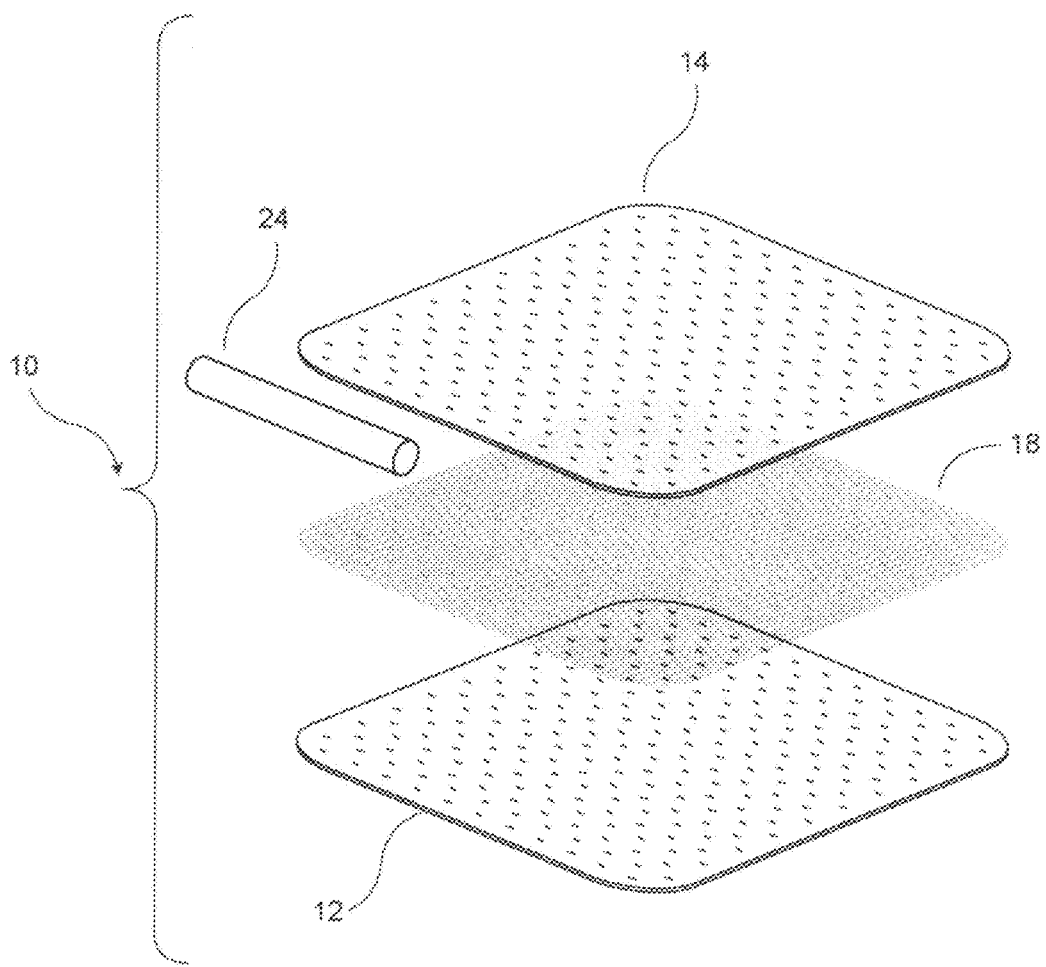
FIG. 4 is an exploded view of one embodiment of the viscera protector.

Polypropylene mesh 18 is completely covered with silicone via a "sandwich" process also known as a "calendering" process and is squeezed by rollers between the two outer silicone layers 12 and 14 which prevent adhesion of the mesh 18 to tissue. The calendering technique is whereby silicone stock is compressed in a multi-roll process into small thicknesses. The silicone then receives polypropylene mesh and is then partially vulcanized by a heated roll and a second layer of silicone is calendered on top to seal the mesh in between the two layers of silicone sheets. As is illustrated in FIG. 5 the polypropylene mesh 18 is completely surrounded by silicone sheets 12 and 14. This sandwiching of the mesh 18 provides structure without promoting in-growth and adhesions common in the use of mesh when placed in the abdominal cavity. Steel dies are used to cut slits 20 through the mesh 18 and silicone layers 12 and 14 to allow fluid to pass through sheets 12 and 14 to provide controlled drainage of exudates.

An alternative embodiment is a perforated silicone sheet, TPE or other bio-compatible material in a single layer without the intermediate mesh layer. Such perforated sheet can be used as abdominal wound dressing for negative pressure wound therapy. It is thin, conformal and can be tucked into the paracolic gutters without the requirement for cutting.

A further embodiment is a perforated silicone sheet, with a mesh strip placed in the middle from top to bottom having a second silicon layer over it. One layer on the body and three layers in the middle of the sheet, which allows the center portion to be anchored with a suture to prevent migration and provides the advantages described above.

We claim:

1. A composite viscera protector consisting of non-adherent silicone outer layers having a thickness of between 0.1 and 2.53 mm are laminated non-adhesively to an intermediate polypropylene mesh layer by a calendering technique wherein the intermediate mesh layer is surrounded by the silicone outer layers and slits sized between 1 and 10 mm are provided in the silicone outer layers and in the intermediate mesh layer.

2. A composite viscera protector as claimed in claim 1 wherein the silicone layers have a thickness of between 0.5 and 2.53 mm.

3. A composite viscera protector as claimed in claim 1 wherein the polypropylene mesh layer has a thickness of between 0.02 and 1.5 mm.

4. A composite viscera protector as claimed in claim 1 wherein the slits are arranged in a pattern that provides reduced forming of troughs in the viscera protector under elastomeric load.

5. A process for producing the composite viscera protector as claimed in claim 1 wherein the silicone outer layers are laminated to the mesh layer by a calendering technique and the slits are sized between 1 and 10 mm by steel dies.

6. A composite viscera protector consisting of non-adherent silicone outer layers having a thickness of between 0.1 and 2.53 mm are laminated non-adhesively to an intermediate polypropylene mesh layer by a calendering technique wherein the intermediate mesh layer is surrounded by the silicone outer layers and slits sized between 1 and 10 mm are provided in the silicone outer layers and in the intermediate mesh layer wherein a tube is provided for draining exudates from the viscera protector.

* * * * *